US010398815B2

(12) United States Patent
Pernot

(10) Patent No.: US 10,398,815 B2
(45) Date of Patent: Sep. 3, 2019

(54) COMPOSITE MATERIAL FOR FILLING CAVITY WOUNDS

(71) Applicants: LABORATORIES URGO, Chenove (FR); VIVATECH, Paris (FR); HCP HEALTHCARE ASIA PTE. LTD, Singapour (SG)

(72) Inventor: Jean-Marc Pernot, Dijon (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 349 days.

(21) Appl. No.: 15/104,324

(22) PCT Filed: Dec. 19, 2014

(86) PCT No.: PCT/FR2014/053446
§ 371 (c)(1),
(2) Date: Jun. 14, 2016

(87) PCT Pub. No.: WO2015/092315
PCT Pub. Date: Jun. 25, 2015

(65) Prior Publication Data
US 2016/0310648 A1 Oct. 27, 2016

(30) Foreign Application Priority Data
Dec. 20, 2013 (FR) .................................. 13 63162

(51) Int. Cl.
*A61F 13/00* (2006.01)
*A61L 26/00* (2006.01)
*A61M 1/00* (2006.01)

(52) U.S. Cl.
CPC ..... *A61M 1/0088* (2013.01); *A61F 13/00017* (2013.01); *A61F 13/00029* (2013.01);
(Continued)

(58) Field of Classification Search
CPC ............. A61L 26/0014; A61L 26/0019; A61L 26/0071; A61L 26/0085; A61F 13/00017;
(Continued)

(56) References Cited

U.S. PATENT DOCUMENTS 5,340,363 A * 8/1994 Fabo ................. A61F 13/00063
424/446
6,270,792 B1 * 8/2001 Guillemet ......... A61F 13/00038
424/443

(Continued)

FOREIGN PATENT DOCUMENTS

| FR | 2783412 A1 | 3/2000 |
| WO | 2009071928 A1 | 6/2009 |
| WO | 2009071938 A1 | 6/2009 |

*Primary Examiner* — Susan S Su
(74) *Attorney, Agent, or Firm* — McAndrews, Held & Malloy, Ltd.

(57) ABSTRACT

The subject of the present invention is a composite wound packing material comprising a casing enclosing a material, or an assembly of materials, forming fluid flow channels, said casing being composed of a self-supporting interface material formed from a thin layer of a composition comprising a hydrophobic matrix and comprising through-holes, said hydrophobic matrix comprising, per 100 parts by weight of a styrene/saturated olefin/styrene triblock copolymer having a viscosity of between 0.2 and 2 Pa·s, as measured in a 10% (weight/weight) solution in toluene, from 400 to 1220 parts by weight of a plasticizer, preferably a plasticizing oil, and from 0 to 720 parts by weight of petroleum jelly, it being specified, moreover, that the total amount of plasticizer and petroleum jelly is greater than or equal to 750 parts by weight and the amount of petroleum jelly is between 400 and 720 parts by weight when the amount of plasticizer is between 1000 and 1220 parts by weight.

19 Claims, 5 Drawing Sheets

(52) U.S. Cl.
CPC .. *A61F 13/00042* (2013.01); *A61F 13/00068* (2013.01); *A61L 26/0014* (2013.01); *A61L 26/0019* (2013.01); *A61L 26/0071* (2013.01); *A61L 26/0085* (2013.01)

(58) Field of Classification Search
CPC .......... A61F 13/00029; A61F 13/00042; A61F 13/00068; A61F 13/0216; A61M 1/0088
USPC ................. 604/304–308, 540–544, 317–326
See application file for complete search history.

(56) References Cited

U.S. PATENT DOCUMENTS

| | | | |
|---|---|---|---|
| 7,930,782 B2 * | 4/2011 | Chen | C08L 53/02 5/636 |
| 2001/0043943 A1 * | 11/2001 | Coffey | A61F 13/02 424/447 |
| 2007/0027414 A1 * | 2/2007 | Hoffman | A61M 1/0088 602/2 |
| 2010/0076363 A1 * | 3/2010 | Staeger Williams | A61L 15/225 602/47 |
| 2010/0262090 A1 * | 10/2010 | Riesinger | A61F 13/00017 604/304 |
| 2012/0294927 A1 * | 11/2012 | Gorka | A61L 15/225 424/445 |
| 2013/0011296 A1 * | 1/2013 | Holm | A61F 13/00042 422/22 |
| 2014/0350496 A1 * | 11/2014 | Riesinger | A61F 13/00068 604/319 |
| 2015/0174285 A1 * | 6/2015 | Auguste | A61L 15/24 424/445 |
| 2016/0143786 A1 * | 5/2016 | Bjork | A61L 15/32 604/307 |

* cited by examiner

COMPOSITE MATERIAL FOR FILLING CAVITY WOUNDS

The present application is filed pursuant to 35 U.S.C. 371 as a U.S. National Phase application of International Patent Application No. PCT/FR2014/053446, which was filed Dec. 19, 2014, claiming the benefit of priority to FR patent application No. 1363162, which was filed on Dec. 20, 2013. The entire text of the aforementioned applications is incorporated herein by reference in its entirety.

The subject of the present invention is a composite wound packing material, especially for packing cavity wounds, which may be used in topical wound treatments which employ negative pressure devices.

In recent years, topical wound treatments which employ negative pressure therapy (NPT) devices have been developed considerably in the field of wound healing, due to their ability to accelerate the duration and quality of wound healing.

The basic principle of NPT treatments is to create a sealed cavity over the wound by means of a thin, flexible sealing film which is adhered to the skin of the patient surrounding the wound. The cavity also makes it possible to insert one end of a suction pipe, the pipe being, for example, sealed onto the sealing film and connected, at its other end, to a vacuum pump capable of creating, inside the cavity, a pressure lower than the ambient atmospheric pressure which surrounds the wound. The negative pressure created inside the cavity affords a number of beneficial therapeutic effects for wound healing, such as, especially, an increase in blood circulation and faster tissue granulation. Different variants of these NTP treatments are currently in existence.

Topical wound treatments which employ negative pressure devices make it possible to treat different types of wounds, from the smallest lesions to the largest cavity wounds, or to burns, irrespective of their size. These injuries may also be deep and consequently have a large volume.

It is necessary to control the manner in which the wound heals. Ideally, the lesion should heal at depth to begin with, and then close up by joining together the edges of the wound in a uniform manner. It is in particular desirable that the wound does not close up at the surface before the deep wound healing has finished, in order to avoid the formation of cavities in the flesh which would become favorable sites for infections. To avoid the formation of these cavities during treatment by NPT, the wound is generally packed by means of a soft or compressible porous material having properties which enable it to withstand the pressure difference created within the wound relative to the ambient atmospheric pressure. The purpose of the material is to hold the edges of the wound far enough apart that they cannot grow and join together to form an undesired cavity.

The material must also make it possible to provide fluid flow channels in order to ensure effective suction of exudates out of the wound, in general into a waste receptacle also referred to as a reservoir, connected to the suction pipe.

The materials used in NPT systems are to be distinguished from conventional multilayer laminar dressings which aim to superficially protect small and substantially planar lesions and are not configured to be introduced within a wound, but simply to be positioned on the surface thereof so as to isolate it from the external environment while wound healing takes place. In particular, laminar dressings do not form fluid flow channels to enable effective drainage of exudates. In addition, the materials constituting these laminar dressings, in particular constituting the outer layer of these dressings, have a certain degree of adhesion to tissues and are not intended to be placed in contact with the wound. Use in a cavity wound would inevitably lead to contact between the material constituting the outer layer of the dressing and the tissues of the wound, which would cause an entirely unacceptable tearing out of newly formed tissue during removal of the dressing.

Most NPT systems sold at the current time use a material based on foam or gauze as wound packing material. However, porous materials of this type have the drawback of promoting tissue growth in their pores, which tissue growth attaches to said pores and, during removal of the material, this may damage the newly formed granulation tissue and be painful for the patient. In addition, such porous materials may also allow exudates to remain in contact with the wound, causing an accumulation of bacteria, leading to infection.

Developments have thus been proposed in order to encase the porous materials of foam or gauze type by materials that are non-porous but that also do not adhere to cutaneous tissues, in contact with which these materials are applied. International applications WO2009/071928 and WO2009/071938 from Smith and Nephew, especially, proposed composite wound packing materials comprising a non-porous casing enclosing a resilient material of foam or gauze type. The casing may additionally be coated or soaked in a non-stick gel such as a hydrogel or a silicone gel. In addition, it is also known practice to apply materials based on gelling fibers in contact with the wound, in planar form. These materials based on gelling fibers and which have the advantage of being non-stick are well known to those skilled in the art and are described for example in patent application WO2006/052839. By way of example of these materials based on gelling fibers, mention may especially be made of carboxymethyl cellulose (CMC) or salts thereof, alginates or else hyaluronic acid. These materials may well constitute the casing of the composite wound packing material. Nonetheless, the materials proposed in application WO2006/052839 have the drawback of separating from one another or delaminating under the effect of the pressure difference applied by the NPT. The use thereof as composite packing material would therefore risk releasing debris into the wound which could eventually become infected and/or disrupt the proper progression of the different steps of the wound healing mechanism.

There is therefore a real need to produce a composite wound packing material, especially for packing cavity wounds, having the desired properties of compressibility and resilience or deformability, while ensuring the flow of exudates without adhering to the cells of the wound, said composite material also having the ability to mechanically withstand the various mechanical stresses, such as the cycles of pressure applied by the NPT, without becoming destructured, and for which the presence of a support for maintaining the gelling material constituting the casing in a native form for as long as possible, is not necessary.

Thus, the subject of the present invention is a composite wound packing material comprising a casing enclosing a material, or an assembly of materials, forming fluid flow channels, said casing being composed of a self-supporting interface material formed from a thin layer of a composition comprising a hydrophobic matrix and comprising through-holes, said hydrophobic matrix comprising:

per 100 parts by weight of a styrene/saturated olefin/styrene triblock copolymer having a viscosity of between 0.2 and 2 Pa·s, as measured in a 10% (weight/weight) solution in toluene;

from 400 to 1220 parts by weight of a plasticizer, preferably a plasticizing oil; and from 0 to 720 parts by weight of petroleum jelly;

it being specified, moreover, that:

the total amount of plasticizer and petroleum jelly is greater than or equal to 750 parts by weight;

the amount of petroleum jelly is between 400 and 720 parts by weight when the amount of plasticizer is between 1000 and 1220 parts by weight.

The casing of the composite material according to the invention preferably consists of a self-supporting interface material, that is to say that it is not necessary to combine it with a support to maintain the shape thereof.

Within the context of the present invention, the term "composite wound packing material" is intended to mean a structure of core/shell type, the core consisting of a material, or an assembly of materials, forming fluid flow channels, the shell, also referred to as the casing, composed of a self-supporting interface material, that is to say that it is not necessary to combine it with a support to maintain the shape thereof.

FIGURES

FIGS. 1A and B are explanatory diagrams of two embodiments of a wound packing material, comprising a casing enclosing a material, or an assembly of materials, forming fluid flow channels (the flow of the exudates being represented, in a purely illustrative manner, by arrows in the figures).

FIG. 2 schematically shows a support for the casing of the composite material according to the invention, said knit having trapezoidal meshes.

HYDROPHOBIC MATRIX

Figure 1A:
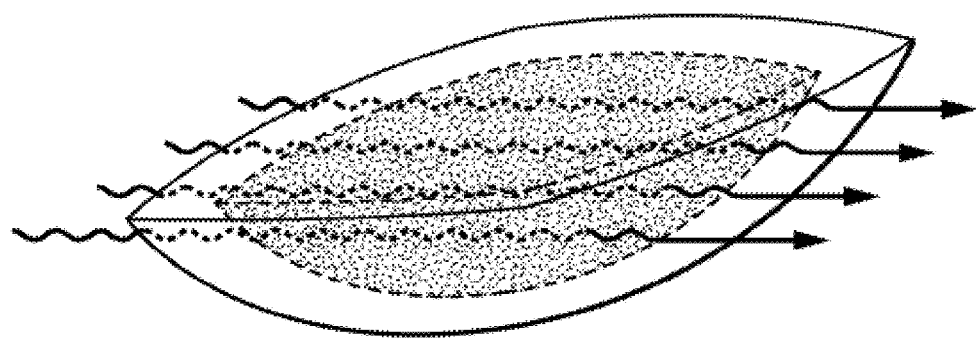

Within the context of the present invention, the casing consists of a self-supporting interface material formed from a thin layer of a composition comprising a hydrophobic matrix.

According to a specific characteristic, the abovementioned hydrophobic matrix also comprises hydrocolloid particles at an amount of less than or equal to 25% by weight relative to the total weight of said hydrophobic matrix.

According to a specific embodiment of the invention, the abovementioned hydrophobic matrix generally consists of an elastomer of styrene/saturated olefin/styrene triblock copolymer type, a plasticizer and optionally petroleum jelly.

This matrix comprises, preferably as the sole elastomer, a triblock block copolymer comprising two styrene thermoplastic end blocks and one elastomeric central block consisting of a saturated polyolefin.

This saturated polyolefin may be of poly(ethylene/butylene) or poly(ethylene/propylene) type.

The triblock copolymers having a saturated central block are well known to those skilled in the art. These compounds have varied properties and differ from one another, in particular, by their viscosity.

It has been discovered that producing a self-supporting material within the meaning of the invention is subject to the choice of a copolymer with a specific viscosity.

Thus, within the context of the present invention, the elastomer will specifically be chosen from copolymers having a high molecular weight, characterized by a viscosity of between 0.2 and 2 Pa·s, as measured in a 10% (weight/weight) solution in toluene.

Triblock copolymers having a saturated central block which correspond to this property are, for example, sold:

by Kraton Polymers under the name KRATON® G1651 or KRATON® G1654 for poly(styrene/ethylene/butylene/styrene) (abbreviated to SEBS) block copolymers;

by Kuraray under the name SEPTON® 52006 for poly(styrene/ethylene/propylene/styrene) (abbreviated to SEPS) block copolymers and SEPTON® 58006 for SEBS block copolymers.

Within the context of the present invention, SEBS or SEPS triblock copolymers having a styrene content of between 25% and 45% by weight relative to the total weight of said copolymer will be preferred.

Preferably, use will be made of the products sold by Kraton Polymers under the names KRATON® G1651 and KRATON® G1654.

To obtain a self-supporting interface material, not only must the nature of the elastomer used be specifically chosen, but also this elastomer will have to be used in specific relative proportions within the hydrophobic matrix, as will be seen below.

The plasticizer used for producing the hydrophobic matrix is intended to improve the properties of stretching, flexibility, extrudability and workability of the abovementioned elastomer.

Preferably, this plasticizer will consist of a liquid or of a mixture of liquids, compatible with the central saturated polyolefin block of the elastomer used.

Among the plasticizers able to be advantageously used, mention may in particular be made of plasticizing oils or else synthetic products based on liquid mixtures of saturated hydrocarbons such as, for example, the products sold by Total under the name GEMSEAL® and in particular the product GEMSEAL® 60 which is an isoparaffinic mixture derived from a completely hydrogenated petroleum cut.

Within the context of the present invention, use will preferably be made of plasticizing oils, preferably plasticizing mineral oils and in particular mineral oils formed from compounds of paraffinic or naphthenic nature or mixtures thereof in variable proportions.

Particularly preferred plasticizing mineral oils are formed from mixtures of compounds of paraffinic and naphthenic nature and in particular such mixtures in which the proportion of compounds of paraffinic nature is predominant.

By way of example of commercial plasticizing mineral oil, mention may be made of the products sold by Shell under the name ONDINA®.

Among these products, excellent results have been obtained with the oils sold under the names ONDINA® 917 or ONDINA® 919.

As indicated above, the amount of plasticizer present within the hydrophobic matrix must be specifically chosen as a function of the amount of elastomer.

Thus, per 100 parts by weight of elastomer, the hydrophobic matrix will contain from 400 to 1220 parts by weight, and preferably from 600 to 900 parts by weight of plasticizer, preferably of a plasticizing oil.

To increase the greasy character and feel of the mixture consisting of the elastomer and the plasticizer, it may be advantageous within the context of the present invention to add a predetermined amount of petroleum jelly to this mixture.

This will preferably be a petroleum jelly in accordance with the French Pharmacopia, available commercially.

The amount of petroleum jelly within the hydrophobic matrix may generally be between 0 and 720 parts by weight, and preferably from 150 to 450 parts by weight, per 100 parts by weight of elastomer.

However, to obtain a self-supporting material suitable for the casing according to the invention, it has been observed that the two following conditions necessarily have to be met:
the total amount of plasticizer and petroleum jelly must be greater than or equal to 750 parts by weight per 100 parts by weight of elastomer;
the amount of petroleum jelly must be between 400 and 720 parts by weight when the amount of plasticizer is between 1000 and 1220 parts by weight.

The hydrophobic matrix which has just been described constitutes the essential element of the compositions making it possible to produce the self-supporting casing of the composite wound packing material according to the invention.

The casing of the composite wound packing material according to the present invention consists of a self-supporting material formed from a thin layer of a composition comprising a hydrophobic matrix and comprising through-holes.

To this end, these compositions comprising a hydrophobic matrix will be formed as a thin layer with through-holes preferably arranged distributed throughout said layer.

The through-holes may be produced by perforation or punching of a composition previously formed into a thin layer, alone or combined with a temporary support or with a protective film, or else by a screened coating on a temporary support. For more details, reference may be made to patent application FR 2 936 158.

Alternatively, the casing of the composite wound packing material in accordance with the invention may be manufactured by hot casting of a composition comprising the hydrophobic matrix as described above on a plate engraved with the pattern used for forming the through-holes, followed by cooling and demolding.

Generally, the casing of the composite wound packing material in accordance with the invention will have a thickness of between 0.4 mm and 2 mm, preferably between 0.5 mm and 1 mm, more preferably still of the order of 0.6 mm.

The through-holes may have any geometry and will have, for example, a circular, rectangular, trapezoidal or square cross section.

Their surface area is generally between 0.25 and 5 $mm^2$.

These holes especially have a mean diameter of between 0.5 and 2 mm, preferably of the order of 1 mm, when their cross section is circular.

These holes are distributed, preferably uniformly, with a density such that the total surface area of the holes represents between 20 and 70%, and preferably between 30 and 50% of the total surface area of the casing.

According to a preferred embodiment, the casing made of self-supporting material according to the invention is in the form of a breathable net (or grid), preferably of square mesh, having:
a thickness of the net of between 0.4 and 2 mm, preferably of between 0.5 mm and 1 mm;
a "yarn width" (width of the space between two consecutive holes) of between 1 and 10 mm;
a grammage of between 200 and 1700 $g/m^2$, and preferably of between 300 and 800 $g/m^2$.

According to a particularly preferred embodiment of the invention, such a self-supporting material will be in the form of a square-mesh breathable net having:
a thickness of the net of 600 microns approximately;
a yarn width of the order of 2 mm;
a grammage of the order of 450 $g/m^2$.

According to an alternative embodiment, the casing consists of a self-supporting interface material formed from a thin layer of a composition comprising a hydrophobic matrix which may optionally be produced from a composition comprising a hydrophobic matrix comprising A parts of a triblock elastomer, B parts of a plasticizing oil, C parts of polyethylene and a hydrocolloid dispersed in a proportion of between 5 and 15% of the total weight of the hydrophobic matrix, with the following relationships:

$A=100$ $300<B<500$ $10<C<50$ $9\%<C/(A+C)<33.5\%$ $1.5\%<C/(A+B+C)<9\%$ $83\%>B/(A+B)>75\%$

Said hydrophobic matrix has through-holes, which may be equated to openings allowing the passage of the wound exudates.

Said hydrophobic matrix has a thickness of between 200 µm and 600 µm, or better still between 300 µm and 500 µm, preferably around 400 µm.

The synthetic hydrophobic thermoplastic elastomer of triblock type is advantageously an elastomer of SIS type formed by copolymerization of polystyrene-type blocks (for example 15%) with isoprene-type blocks. The elastomer preferably has an intermediate or high molecular weight and the diblock content thereof is for example 18%.

The polyethylene is provided in granular form. The Brookfield viscosity thereof is around 450 cP at 140° C. and the melting point thereof is between 92° C. and 122° C.

The plasticizer of the composition is oil, especially a mineral or vegetable oil compatible with the other elements of the composition and tolerated by the skin. Use is preferably made of a low-viscosity paraffin oil based on paraffinic and naphthenic compounds or mixtures of paraffin oil.

The plasticized composition is extensible and "elastic" and has a certain degree of hysteresis, with an elastic recovery of at least 3-5% for an elongation of 20%.

To increase the non-stick nature and to maintain, at the interface, a moist environment which promotes wound healing, a hydrocolloid in dispersion is added to the matrix consisting of the elements defined above. Reference may be made to the abovementioned document EP 1 143 895 which defines the nature of, and the conditions for, addition of a hydrocolloid which is also suitable in the present invention. In practice, use will preferably be made of sodium carboxymethyl cellulose (NaCMC) in proportions of from 5% to 15% of the hydrophobic matrix.

Naturally, the composition may also contain various antioxidant or stabilizing products, and also active principles which will add a specific effect to the composition. These products are known to those skilled in the art.

The manufacture of the interface in accordance with the invention begins with hot-blending without solvent according to the "hot melt" technique (at a temperature of approximately 150° C.) of the triblock polymer, the oil-based component and the polyethylene so as to obtain a homogenous mixture, into which the CMC is incorporated at a slightly lower temperature, for example, of from 130° C.-135° C.

The product of the mixing is then deposited by coating at a chosen thickness onto a support.

The support may be a continuous or discontinuous support; it is an intermediate support serving for the transport and storage of the interface until it is used in the form of casing for composite wound packing material. The support may be of any nature, as long as it has a non-stick surface making it possible to easily separate the interface and the support. Said support is advantageously a flexible support such as a silicone-based sheet (film, liner), for example a sheet of silicone polyester. Either virtually at the same time, or during a subsequent step, another silicone-based sheet is added above the interface, such that the latter is protected on both its faces. Reference may be made, for a technique for coating between two supports, to the figure on page 153 of the work "Coating and Laminating Machines" by Herbert Weiss, Converting Technology Co., 1977.

According to a fundamental aspect of the invention, the method provides the formation of holes in the coated interface. According to a first embodiment, the holes are made by a method for perforating (for example by punch and die) the coating when it has already been deposited on its flexible support, and preferably while it is protected by its two flexible support and protection sheets.

According to a second embodiment, the holes are formed in the coating at the same time as the latter is deposited onto its support, for example by a machine sold by Cavitec under the name Cavimel-TSM or by Nordson under the name System REA, this method automatically laying the coating in screen form. The principle is to deposit the product onto a screen cylinder or etched cylinder by means of a nozzle, which cylinder then transfers the screened coating onto its support. Such a method is known for example from document WO/011352.

The holes have a mean diameter of from 1 to 4 mm, for example in the form of 3 mm round holes with a pitch of 8 mm.

Said hydrophobic matrix has a tacky capacity which excludes any notable adhesiveness in the measurable sense of the term, the interface of the invention specifically being non-tacky and not causing any tearing of human tissue or of newly formed tissue during removal thereof.

According to a second alternative embodiment, a non-absorbent hydrophobic elastomer matrix is most particularly suitable for use of a packing material for cavity wounds which is the subject of said invention.

This matrix is described in Lohmann & Rauscher patents EP 2 524 706 and EP 2 524 705, the contents of which are entirely incorporated by reference into the present description.

According to this second alternative embodiment, the hydrophobic elastomer matrix may comprise at least one synthetic triblock elastomer of general formula A-B-A, the end block A possibly being of polystyrene type and the central block B possibly being of saturated polyolefin type.

To obtain a hydrophobic elastomer matrix according to this second alternative embodiment, triblock elastomers of polystyrene-b-poly(ethylene-butylene)-b-polystyrene (S-EB-S) type, or polystyrene-b-poly(ethylene-propylene)-b-polystyrene (S-EP-S) type, or polystyrene-b-poly(ethylene-ethylene/propylene)-b-polystyrene (S-EEP-S) type, with high and ultra-high molecular weights are used.

Advantageously, hydrated polystyrene-b-poly(ethylene-butylene)-b-polystyrene (S-EB-S, for example Kraton G1651) elastomers are used. Hydrated polystyrene-b-poly(ethylene-ethylene/propylene)-b-polystyrene (S-EEP-S, such as Septon 4033, 4055, 4077 or 4099) elastomers may also be used.

To obtain a hydrophobic elastomer matrix according to this second alternative embodiment, a mixture of at least two triblock elastomers of S-EB-S or S-EP-S type, in particular of S-EEP-S type, is preferably chosen, one of the two elastomers having a high molecular weight, that is to say a molecular weight of greater than 150 000 Daltons and less than 300 000 Daltons as measured by size exclusion chromatography, and the other elastomer having an ultra-high molecular weight, that is to say a molecular weight of greater than 300 000 Daltons and less than 600 000 Daltons as measured by size exclusion chromatography, and each having a Brookfield viscosity of at least 5000 mPas (measured in a 10% toluene solution at 30° C.).

The hydrophobic elastomer matrix may comprise between 1.5 and 10% by weight of elastomers, preferably between 2 and 3% and even more preferably 2.6%.

Thus, a matrix comprising a combination of an elastomer from the Kraton brand, such as Kraton G1651 or another elastomer from the G series of the Kraton brand having the desired molecular weight properties, with an elastomer from the Septon brand, such as the Septon 4055 elastomer, the Septon 4077 elastomer or the Septon 4099 elastomer, is envisioned by this embodiment.

In another advantageous manner, the hydrophobic elastomer matrix comprises two elastomers with ultra-high molecular weight, that is to say with molecular weight of greater than 300 000 Daltons and less than 600 000 Daltons as measured by size exclusion chromatography.

Thus, a matrix comprising a combination of an elastomer from the Septon brand, such as the Septon 4055 elastomer, with another elastomer from the Septon brand such as Septon 4077 or else the Septon 4099 elastomer, is envisioned by this embodiment. A combination of a Septon 4077 elastomer with a Septon 4099 elastomer is also envisioned.

It should be noted that, within the hydrophobic elastomer matrix, the total share of elastomer having the higher molecular weight is greater than 5%, preferably greater than 10%, while being less than 50% of the total share of elastomers introduced into the matrix.

Aside from the triblock elastomer(s), the hydrophobic polymer matrix also comprises at least one oil-based plasticizer, preferably constituting the majority of the hydrophobic elastomer matrix. The oil-based plasticizer may especially consist of a plasticizing oil and/or petroleum jelly. Due to the combination of a high proportion of oil-based plasticizer with a very low proportion of triblock elastomers, the matrix behaves like a pure fatty substance, such that it has very good compatibility with tissues and very good properties of not adhering to the wound.

Among the oil-based plasticizers suitable for constituting the hydrophobic matrix according to this second embodiment, that is to say enabling the plasticization of the elastomer, mention may be made of paraffin oils, medical white oils, mineral oils, petroleum jelly, balm paraffins, silicone oils, waxes, or else mixtures thereof.

Preferably, the plasticizer will consist of a liquid or of a mixture of liquids, compatible with the central saturated polyolefin block of the elastomer used.

Among the plasticizers able to be advantageously used, mention may in particular be made of plasticizing oils or else synthetic products based on liquid mixtures of saturated hydrocarbons such as, for example, the products sold by Total under the name GEMSEAL® and in particular the product GEMSEAL® 60 which is an isoparaffinic mixture derived from a completely hydrogenated petroleum cut.

Within the context of the present invention, use will preferably be made of plasticizing oils, preferably plasticizing mineral oils and in particular mineral oils formed from compounds of paraffinic or naphthenic nature or mixtures thereof in variable proportions.

Particularly preferred plasticizing mineral oils are formed from mixtures of compounds of paraffinic and naphthenic nature and in particular such mixtures in which the proportion of compounds of paraffinic nature is predominant By way of example of commercial plasticizing mineral oil, mention may be made of the products sold by Shell under the name ONDINA®.

Among these products, excellent results have been obtained with the oils sold under the names ONDINA® 917 or ONDINA® 919.

The matrix may also contain antioxidants. As suitable antioxidants, mention may be made of antioxidants containing sulfur, for example zinc dibutyldithiocarbamate, sold under the name PERKACIT ZDBC by Akzo Nobel Chemicals, and/or antioxidants containing phenol, for example the products sold under the name IRGANOX® 1010, IRGANOX® 565 and IRGANOX® 1035 by BASF.

Within the context of the present invention, the compound IRGANOX®1010 is preferred.

The hydrophobic elastomer matrix according to this second alternative embodiment may also comprise an additive selected from the group consisting of stabilizers, extrusion aids, fillers, pigments, dyestuffs, crosslinking agents, anti-odorants, adhesion agents, compatibilizing agents and combinations thereof.

In addition, said matrix may comprise at least one type of organic or inorganic water-fixing hydrophilic particles such as hydrocolloids or superabsorbent polymers. Among the latter, mention may be made of carboxymethylcellulose, alginates, xanthans, gelatins, pectins, and derivatives thereof.

An active agent may also be added within this matrix. Preferably, a biguanide, such as metformin or polyhexamethylene biguanide (PHMB), or else PHMB stearate, will be added to said matrix.

This matrix may be defined as a non-absorbent hydrophobic elastomer matrix.

According to this second alternative embodiment, "non-absorbent" hydrophobic elastomer matrix is intended to mean any hydrophobic elastomer matrix as described above which absorbs less than 35% of a saline solution (0.8% NaCl solution) in 24 h relative to the dry weight of the matrix.

According to a variant of this embodiment, said matrix may be used alone as casing, or may coat a support as defined below, to constitute said casing.

Casing Support

According to one of the features of the invention, and with the proviso that this does not adversely affect the good cohesive properties of the composite material according to the invention, the casing composed of a self-supporting interface material may comprise a support formed from a fabric of yarns made of flexible, barely extensible and non-elastic material.

This support is in the form of a fabric having wide, open meshes and may be obtained by weaving or knitting processes allowing square or polygonal open meshes of uniform size to be formed. In the case of a woven fabric, the meshes may be fixed by means of turning yarns so as to obtain good dimensional stability. The size of the meshes is such that the unit area of the apertures is of the order of 0.5 to 10 mm$^2$, preferentially 0.5 to 3 mm$^2$, the aperture ratio of the fabric (the ratio of the open surface area to the total surface area) being of the order of 50 to 90%. The yarn used for manufacturing the fabric is preferentially a continuous filamentous yarn which is barely extensible and non-elastic, the extensibility or elongation being less than 35%. The term "continuous filamentous yarn" is intended to mean a yarn formed from one or more long twisted filaments; the choice of long filaments makes it possible to avoid short fibers which run the risk of becoming detached from the support and dispersing close to the area of contact with the wound.

For the same reason, the material which constitutes the yarns is preferably of the hydrophobic type and of artificial or synthetic nature; these constituents, such as, for example, polyesters, polyamides and cellulose acetates, make it possible to obtain long filaments and yarns having far fewer fibrils than the yarns obtained, for example, from short fibers. The choice of certain synthetic materials, such as polyesters, also gives the possibility of heat-setting the wide-mesh structure of the support. The wide-mesh fabric is preferentially produced using yarns of the same nature, but it is also possible to use fabrics manufactured, for example, using warp yarns and weft yarns which are different in nature. Finally, another advantage of the non-elastic, barely extensible materials, such as polyesters, is the easier working during the process of covering the yarns of the fabric with the material constituting the casing.

According to a preferred embodiment of the invention, the self-supporting interface material is applied to the wide-mesh fabric so as to coat the yarns of the fabric while leaving the majority of the meshes unobstructed.

As indicated above, a woven or knitted support having wide rectangular, square or polygonal meshes, the aperture of which corresponds substantially to 4 to 20 meshes per cm, is used, the fabric having an aperture ratio (ratio of the open surface area to the total surface area) of 50 to 90%. The yarn used to obtain the support is preferably a continuous filamentous yarn, and to produce the preferred examples of the invention, yarns made of artificial or synthetic material, with hydrophobic character and extensibility of less than 35%, are chosen.

The nature of the yarn is, for example, a polyester of polyethylene terephthalate type, a polyamide or a cellulose acetate; use is preferably made of a fabric with wide, heat-set meshes made of continuous polyester yarns (Tergal or polyethylene terephthalate), for example the fabrics sold under the name of marquisette, with a grammage of approximately 30 to 80 g/m$^2$. These fabrics, which are virtually non-extensible in the warp and weft directions, have the advantage of being easier to work with than elastic fabrics, and more uniform coating of the yarns is obtained.

This type of support, formed from a fabric of yarns made of flexible, barely extensible and non-elastic material, is especially described in patent application WO 00/16725.

Alternatively, the fabric constituting the support for the casing may be a heat-set knit with weft yarns, said yarns being continuous yarns comprising non-elastic filaments, which has an extensibility in the transverse direction, measured according to standard NF EN 13726-4, of between 0.01 and 0.5 N/cm, preferably of between 0.05 and 0.3 N/cm and more preferably still of between 0.08 and 0.15 N/cm.

According to a preferred version of the present invention, this knit will have an extensibility in the longitudinal direction, measured according to the same standard, of between 15 and 30 N/cm and preferably of between 20 and 25 N/cm. Such extensibility in the longitudinal direction enables easier and more uniform coating of the knit by the self-supporting interface material, from an industrial viewpoint.

Generally, this knit is made with weft yarns, and will in particular be manufactured according to the "cast-off stitch" technology.

Furthermore, this knit is heat-set. This heat-setting makes it possible to dimensionally stabilize the structure of the knit after knitting via a thermal effect. This heat-setting operation is commonly used by those skilled in the art in the manufacture of a knit of which it is desired to fix the three-dimensional structure. It can be carried out using various technologies, either by passing the knit through a series of thermoregulated ovens, or by passing the knit through an autoclave, or else by passing the knit between one or more heated rolls. In the context of the present invention, preference will be given to carrying out this heat-setting operation by passing the knit between two heated rolls.

According to the invention, this knit is produced using continuous yarns comprising non-elastic filaments. The term "continuous yarn comprising filaments" is intended to mean a yarn formed from one or more long twisted filaments.

This yarn will preferably be chosen from yarns of 33 to 115 dtex comprising 12 to 36 filaments.

The constituent material of the yarns is preferably synthetic and hydrophobic in nature. This material is advantageously chosen from polyesters and polyamides.

According to the preferred version of the invention, use will be made of a heat-set knit with weft yarns based on 50-dtex polyester continuous yarns comprising 24 filaments.

This knit may have a grammage of between 20 and 40 g/m$^2$ and preferably between 24 and 32 g/m$^2$.

This knit may have rectangular, square or polygonal meshes.

These meshes will advantageously have apertures, the unit area of which before coating is of the order of 0.5 to 3 mm$^2$ and preferably between 0.85 and 1.25 mm$^2$ According to a preferred embodiment, a knit which has trapezoidal meshes will be used.

According to a preferred version of the present invention, a knit which has trapezoidal meshes will be used. A knit with such a mesh is illustrated schematically in FIG. 2. The angle α is defined as the average join angle of the rows (1) and the columns (2) of the knit.

According to the preferred version of the present invention, this knit has an average mesh surface area of the order of 0.95 mm$^2$ and an angle α as described in FIG. 1 of between 75 and 85 degrees.

The coating of the cohesive gel onto the knit is carried out so as to leave the meshes essentially unsealed, according to techniques known to those skilled in the art and so as to obtain a coating which ranges from 110 to 160 g/m$^2$ and preferably from 125 to 135 g/m$^2$.

In the context of the present invention, the process described in patent application WO 00/16725 will preferably be carried out in order to perform this coating.

Figure 2:
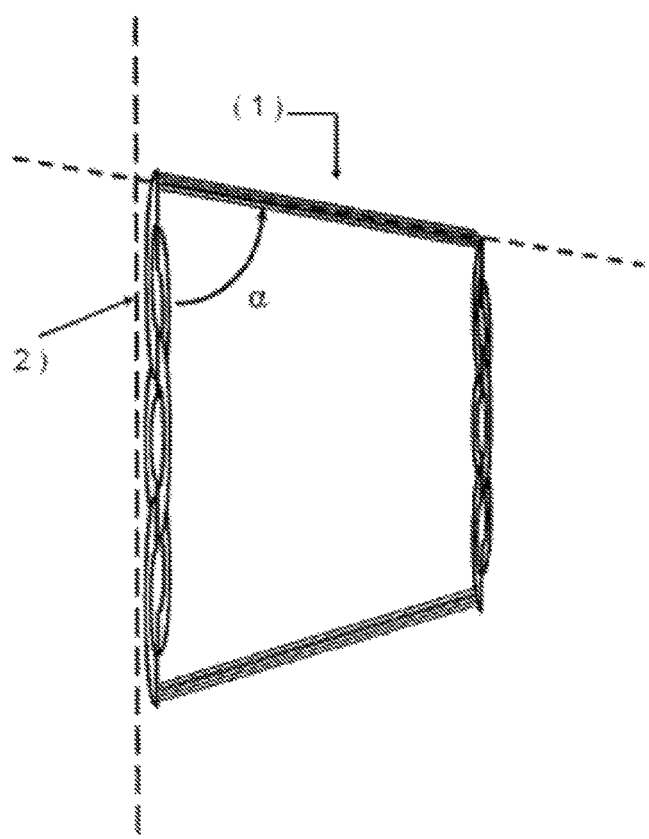

The appended FIG. 2 represents, schematically, a mesh of the fabric of a dressing according to a preferred embodiment of the invention.

According to a second alternative embodiment, the casing composed of a self-supporting interface material may comprise another type of support formed from an open-mesh fabric consisting of barely extensible and barely elastic yarns. These yarns are preferably made of polyester. They are multifilament woven yarns of a diameter of between 10 and 20 μm and preferentially of approximately 16 μm. The mesh aperture is between 1 and 1.1 mm$^2$ and preferably approximately 1.05 mm$^2$ This support preferably has 7 yarns per cm in the longitudinal direction, and 8 yarns per cm in the transverse direction. The grammage of this support is between 40 and 45 g/cm$^2$ and is preferably approximately 43 g/cm$^2$. Finally, its extensibility at 20% was measured according to standard NF EN 13726-4. The latter is between 20 and 30 N/cm in the longitudinal direction, and is preferentially 24 N/cm. Similarly, this extensibility in the transverse direction is between 1 and 5 N/cm and preferably 3 N/cm.

Material, or Assembly of Materials, Forming Fluid Flow Channels

The composite wound packing material according to the present invention comprises a casing described above enclosing a material, or an assembly of materials, forming fluid flow channels, more particularly wound exudate flow channels.

The materials introduced into the casing of the composite material according to the invention may be porous or non-porous, compressible or non-compressible, deformable or non-deformable, resilient or non-resilient, as long as they perform their function of forming, intrinsically and/or by arranging them in relation to one another, fluid flow channels.

Within the meaning of the present application, "porous material" is intended to mean any material, the structure of which has cavities which may form fluid flow channels.

"Compressible material" is intended to mean any material, the volume of which decreases and the shape of which is modified under the effect of an external physical stress.

"Deformable material" is intended to mean any material, the shape of which is modified under the effect of an external physical stress, but the volume of which remains constant.

"Resilient material" is intended to mean any compressible or deformable material having the property of returning to its initial volume and/or its initial shape once the external physical stress has been removed. In other words, resilient material is intended to mean a material with shape memory.

The composite material of the present invention consists of a "casing enclosing a material, or an assembly of materials", that is to say it is in the form of a structure of core/shell type, the core consisting of a material, or an assembly of materials, forming fluid flow channels, the shell, also referred to as the casing, composed of a self-supporting interface material. It should be noted that the shell completely encloses the material, or the assembly of materials, forming fluid flow channels. The material(s) forming fluid flow channels may have a greater or lesser mobility within the casing. Such structures are depicted schematically in FIGS. 1A and B.

According to a first preferred embodiment, the casing encloses a (single) material forming fluid flow channels. In this embodiment, the material is porous, compressible and resilient. The porosity of the material confers upon it the property of forming fluid flow channels intrinsically, due to the properties and the nature of the material used, having fluid flow channels within its structure.

According to this first embodiment, the casing may enclose a (single) material combining various properties, that is to say which may be porous or non-porous, compressible or non-compressible, deformable or non-deformable, resilient or non-resilient, as long as it performs its function of forming fluid flow channels intrinsically.

This first embodiment can be seen in FIG. 1A, in which the fluid flow channels allow exudates to pass through as illustrated in a schematic and purely illustrative manner by arrows in the figure.

According to a second preferred embodiment, the casing encloses an assembly of materials forming fluid flow channels.

In this second embodiment, the materials are separate from one another within the casing and separated by one or more interstices which may constitute fluid flow channels.

In this second embodiment, the materials may, according to a first preferred aspect, be porous, compressible and resilient. The fluid flow channels may then be formed both by the intrinsic porosity of the materials constituting the assembly, and by the interstices present between the different materials. Since the materials are compressible and resilient, and are also able to move with respect to one another within the casing, the assembly of these materials is also compressible and resilient.

Alternatively, in this second embodiment, the materials may, according to a second preferred aspect, be non-porous, non-compressible and non-deformable. The fluid flow channels are then formed solely by the interstices present between the different materials. The fluid flow channels allow exudates to pass through as illustrated in a schematic and purely illustrative manner by arrows in FIG. 1B. The non-compressible and non-deformable materials may move with respect to one another within the casing, thereby conferring upon the assembly of these materials a deformable character.

Figure 1B:
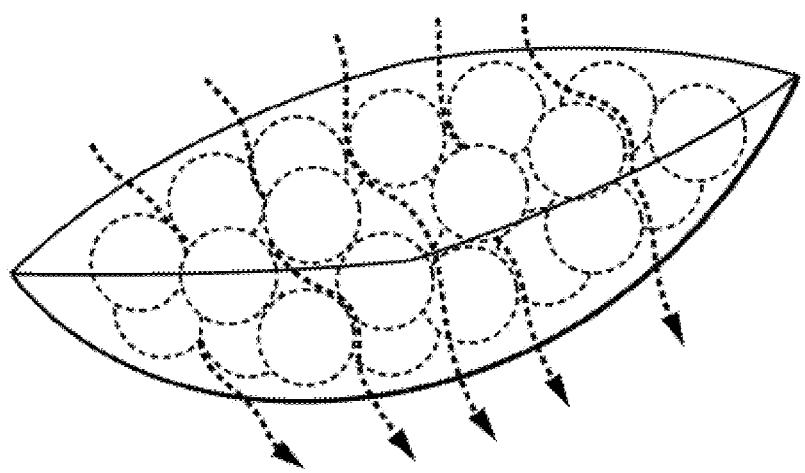

This second embodiment can be seen in FIG. 1B.

According to a specific alternative, it is entirely possible to envision providing a combination of said materials mentioned above. Thus, it is possible to combine, according to an embodiment of the invention, materials which are porous or non-porous, compressible or non-compressible, resilient or non-resilient and deformable or non-deformable, thus constituting an assembly of materials forming fluid flow channels. The intrinsic properties of each porous material, having inherent fluid flow channels because of its structure, and the properties conferred by an assembly of porous or non-porous materials, are of course retained in this type of combination. Thus, fluid flow channels may be both formed by the intrinsic porosity of a material and also by the interstices separating different materials arranged in an assembly, especially if the latter are able to move with respect to one another.

The porous, compressible and resilient material for filling the casing may, for example, comprise one or more foams or gauzes, but also any other suitable material having the required physical characteristics may be used as material for filling the casings. By way of example of porous, compressible and resilient material for filling the casing, mention may be made of polyurethane foams, foams based on poly(vinyl alcohol) or else based on cellulose, or on starch, or indeed various textile products based on synthetic or natural fibers chosen from the non-limiting list of compounds consisting especially of cotton, linen, wool, silk, chlorofibers, polyester, polyolefins, preferentially polyethylene, or else polyacrylic or polyamide fibers, in any form, whether thread, fiber, knit, woven, nonwoven or fabric, etc.

This material for filling the casing must be both compressible and also hard enough to hold the cutaneous tissues apart in the wound bed without being too aggressive for the tissues.

The porous material for filling the casing may thus have a hardness ranging from 5 to 100 Shore A and preferentially from 20 to 100 Shore A.

The non-porous, non-compressible and non-deformable materials for filling the casing may, for example, be chosen from PMMA (poly(methyl methacrylate)), glass, polystyrene, PVC, acrylonitrile butadiene styrene (ABS), silicone, SAN (styrene acrylonitrile), polyurethane, polyvinyl alcohol, cellulose, polyester, polyolefins, polyethylene, or a mixture of these materials. According to a preferred embodiment, the non-porous, non-compressible and non-deformable materials for filling the casing may be chosen from glass beads, polystyrene beads, silicone beads or polyethylene beads.

Active Agents

Various compounds may also be added to the casing and/or to the filling material of the composite materials of the present invention, such as, in particular, active agents or adjuvants commonly used in the field of wound treatment or in the pharmacological field.

The composite material may contain active principles that have a favorable role in wound treatment. These active principles may especially induce or accelerate wound healing. Other active agents may also be used within the context of the invention, such as, for example, bactericidal or bacteriostatic agents, antiseptics, painkillers or local anesthetics, anti-inflammatories, antipruritics, calmatives, hydrating agents, antioxidants, dipigmenting agents and mixtures thereof.

Generally, these active agents may be chosen from:

active agents promoting wound healing, such as Retinol, Vitamin A, Vitamin E, N-acetyl-hydroxyproline, *Centella asiatica* extracts, papain, silicones, thyme, niaouli, rosemary and sage essential oils, hyaluronic acid, allantoin, -Hema'tîte (gattefossé), Vitamin C, TEGO Pep 4-17 (evonik), Toniskin (silab), Collageneer (Expanscience), Timecode (Seppic), Gatuline skin repair (gattefossé), Panthenol, PhytoCellTec Alp Rose (Mibelle Biochemistry), Erasyal (libragen), Serilesine (Lipotec), Heterosides of Talapetraka (Bayer), Stoechiol (codif), Macarose (Sensient), Dermaveil (Ichimaru Pharcos), Phycosaccaride AI (Codif), growth factors, metformin, synthetic polysulfated oligosaccharides having 1 to 4 monosaccharide units, such as sucrose octasulfate potassium salt (known by the abbreviation KSOS, sold in the product Urgotul® Start by Laboratoires Urgo;

bactericidal or bacteriostatic agents such as polymyxin B, penicillins (amoxycillin), clavulanic acid, tetracyclines, minocycline, chlortetracycline, aminoglycosides, amikacin, gentamicin, neomycin, probiotics, silver salts such as silver sulfate, silver chloride, silver nitrate, silver sulfadiazine, quaternary ammoniums, polyhexamethylene biguanide and chlorhexidine;

antiseptics, such as thiomersal, eosin, chlorhexidine, phenylmercuric borate, aqueous hydrogen peroxide solution, Dakin's solution, triclosan, biguanide, hexamidine, thymol, Lugol's solution, iodinated povidone, merbromin, benzalkonium chloride, benzethonium chloride, ethanol or isopropanol;

painkillers or local anesthetics such as paracetamol, codeine, dextropropoxyphene, tramadol, morphine and its derivatives, or corticoids and derivatives;

anti-inflammatories, such as glucocorticoids, nonsteroidal anti-inflammatories, aspirin, ibuprofen, ketoprofen, flurbiprofen, diclofenac, aceclofenac, ketorolac, meloxicam, piroxicam, tenoxicam, naproxen, indomethacin, naproxcinod, nimesulide, celecoxib, etoricoxib, parecoxib, rofecoxib, valdecoxib, phenylbutazone, niflumic acid or mefenamic acid;

depigmenting agents, such as kojic acid (Kojic Acid SL®—Quimasso (Sino Lion)), arbutin (Olevatin®—Quimasso (Sino Lion)), the mixture of sodium palmitoyl proline and of European water lily extract (Sepicalm®—Seppic) or undecylenoylphenylalanine (Sepiwhite®—Seppic);

antipruritics: hydrocortisone, enoxolone, diphenhydramine, locally applied anti-H1 antihistamine;

moisturizing active agents, such as Xpermoist (Lipotec), hyaluronic acid, urea, fatty acids, glycerol, waxes or Exossine (Unipex);

UV-screening agents, such as Parsol MCX or Parsol 1789;

calmatives, such as camomile, bisabolol, xanthalene, glycyrrhetinic acid, tanactin (CPN) or Calmiskin (Silab);

antioxidants, such as vitamin E

According to a preferred embodiment, the active agents which may be introduced into the casing and/or into the filling material of the composite materials according to the present invention are preferably chosen from active agents which promote wound healing, anti-inflammatories and mixtures thereof.

"Active agent which promotes wound healing" is intended to mean any active agent capable of acting favorably at any stage of the wound healing process via any sort of interaction, that is to say via any interaction of biological, chemical or physical nature, with the wound in contact with which said active agent is applied.

More particularly, the active agents which may be introduced into the casing and/or into the filling material of the composite materials according to the present invention are preferably chosen from metformin, synthetic polysulfated oligosaccharides having 1 to 4 monosaccharide units, such as in particular sucrose octasulfate potassium salt, aspirin, silver sulfate, silver sulfadiazine and mixtures thereof.

Generally, the composite materials according to the present invention may comprise active agents in the casing and/or in the filling material at an amount of from 0.01 to 20% by weight, preferably from 1 to 15% by weight and more preferably still from 2 to 10% by weight, relative to the total weight of the casing and/or of the filling material containing them.

As adjuvants, mention may be made of dyestuffs, fillers, odor absorbers or trappers, pH regulators, microcapsules or microspheres that may optionally contain active agents, vaseline, polymers or surfactants making it possible to optimize the gelling rate, wettability or release of the active agents of the composite material.

The composite wound packing material according to the invention may be in any desired geometric shape, especially adapted to the shape and depth of the wound.

The casing is preferably closed around the material, or an assembly of packing materials, forming fluid flow channels, by heat sealing, by stitching or by one or more knots at the level of the casing, preferentially by heat sealing.

According to a particular embodiment, one or more porous, compressible and elastic filling materials may be introduced into the same casing.

According to a particular embodiment, the assembly of materials forming fluid flow channels may be in the form of a "pearl necklace", that is to say that several filling materials forming fluid flow channels may be distributed individually in as many cavities of the nonwoven casing, separated from one another by heat sealing, by stitching or by one or more knots at the level of the casing, preferentially by heat sealing of said casing.

The present invention is illustrated in more detail in the following non-limiting example.

EXAMPLE

Aim:

The mechanical strength (especially with regard to destructuring) of various composite wound packing materials was tested under conditions close to those of NPT (that is to say, under vacuum at 125 mmHg), in order to observe, among the various materials tested, which withstand the force exerted and which break.

The following apparatus and solution were used:
a MECA-004/SYN200 dynamometer, capable of applying a force of 26 N on contact with the desired material;
a 100N/MECA-008 sensor adjacent to the dynamometer;
a polished steel round-tipped metal rod of diameter 25.3866 mm and with circularity at the equator of 0.0093 mm;
an annular (gripping) clamp with an internal diameter of 44.4763 mm;
an $NaCl/CaCl_2$ solution comprising NaCl (8.298 g +/−5%) and $CaCl_2$ (0.368 g +/−5%).

A self-supporting interface material formed from a thin layer of a composition comprising a hydrophobic matrix and comprising through-holes was tested, said hydrophobic matrix comprising:
per 100 parts by weight of a styrene/saturated olefin/styrene triblock copolymer having a viscosity of between 0.2 and 2 Pa·s, as measured in a 10% (weight/weight) solution in toluene;
from 400 to 1220 parts by weight of a plasticizer, preferably a plasticizing oil; and
from 0 to 720 parts by weight of petroleum jelly;
it being specified, moreover, that:
the total amount of plasticizer and petroleum jelly is greater than or equal to 750 parts by weight;
the amount of petroleum jelly is between 400 and 720 parts by weight when the amount of plasticizer is between 1000 and 1220 parts by weight, said interface material constituting a potential casing for the composite wound packing material according to the invention.

A hydrophobic crosslinked polyurethane foam sold by AQF® under the trade name PDQZ30 was used as material forming fluid flow channels.

Operating Procedure

Force to Apply to the Samples

The NPT systems are regulated in the most common way to apply a vacuum of 125 mm Hg. This corresponds to the application of a force of 26 N to the composite wound packing material.

Sample Preparation 3 square samples with 80 mm side lengths are cut using a punch from AQF PDQZ30 foam constituting the material for filling the casing.

1 square sample of 80 mm side length was also cut using a punch from the self-supporting interface material constituting the casing to test.

In parallel, a test solution comprising NaCl (8.298 g +/−5%) and $CaCl_2$ (0.368 g +/−5%) was prepared. This solution makes it possible, on the one hand, to simulate the moisture conditions found within a wound and, on the other hand, to simulate the saline concentration of the exudates found in a wound.

Finally, the square of self-supporting interface material constituting the casing to be tested was soaked in the test solution for 30 minutes at 37° C.+2° C. After 30 minutes, the square was removed and left to drip dry for approximately 30 seconds.

Figure 3:
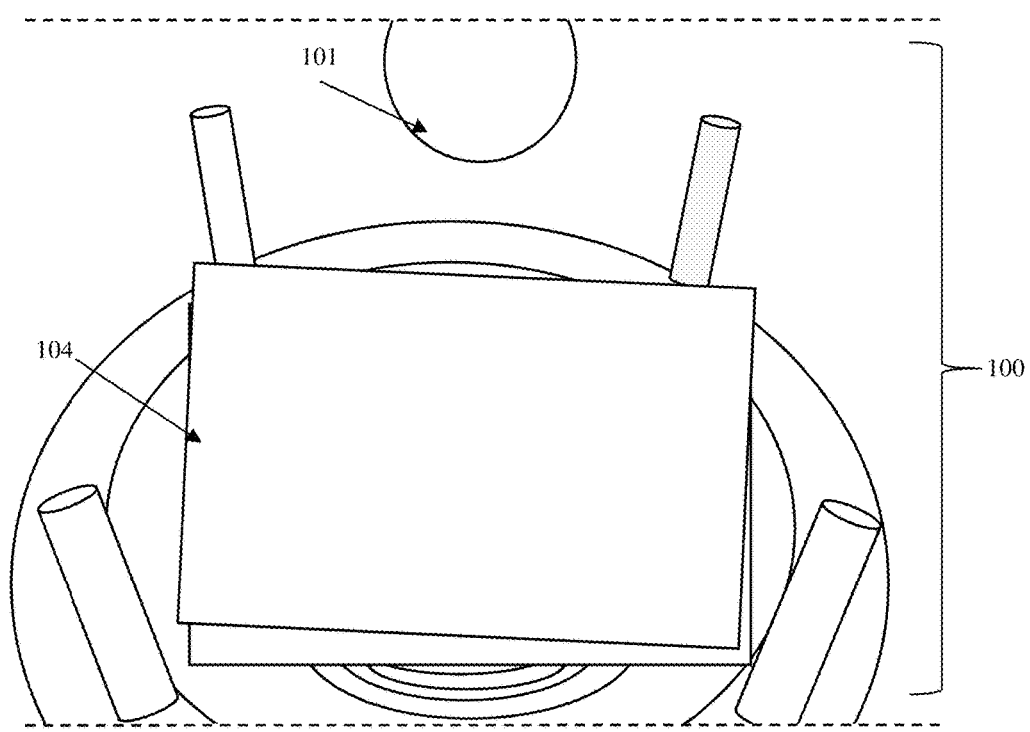
FIG. 3 illustrates the assembly of the device 100 used to carry out the mechanical strength test used in the examples according to the invention.

The square of hydrated self-supporting interface material was then superposed on the square of foam (which is not hydrated), then the composite material obtained in this way was positioned in the test device. FIG. 3 illustrates the test device 100 on which the sample of composite material 104 consisting of the superposed square of foam and the self-supporting interface material was deposited.

Figure 4:
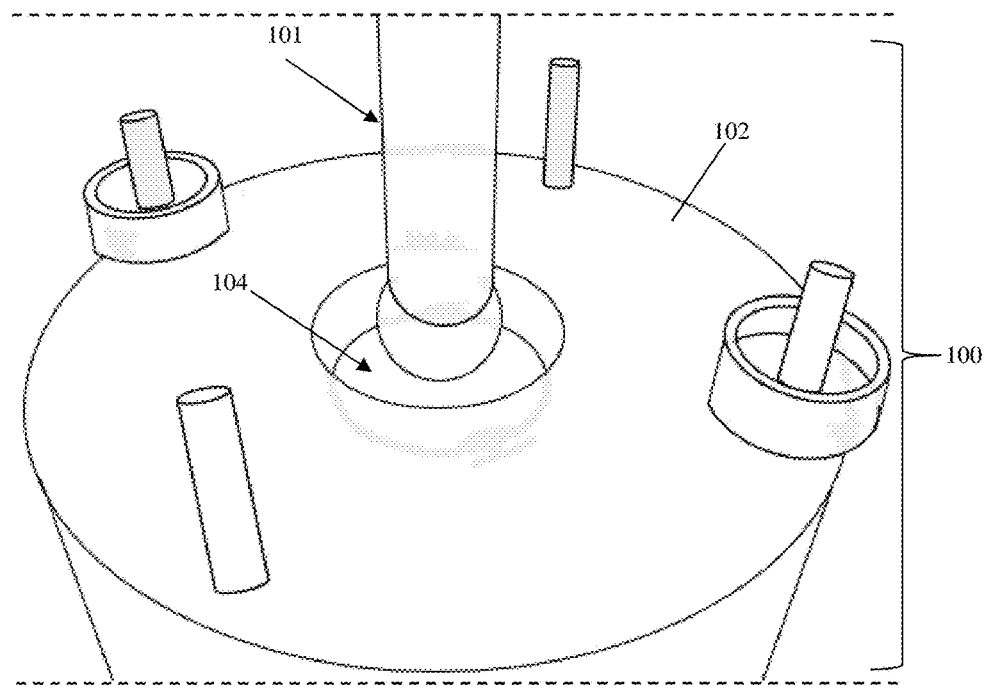
FIG. 4 illustrates of the assembled device 100 used to carry out the mechanical strength test used in the examples according to the invention.

An annular gripping clamp 102 is then affixed to the sample consisting of the composite material 104 and is fixed by means of 4 clamping screws so as to ensure complete cohesion between the two materials. FIG. 4 illustrates the device 100 after putting the gripping clamp 102 in place.

The dynamometer is regulated such that the vertical falling speed of the round-tipped metal rod 101 corresponds to (300+10) mm/min and such that this fall is stopped when the round-tipped metal rod 101 applies a force of 26 N after having come into contact with the sample. After contact and application of the desired pressure to the sample, the round-tipped metal rod 101 stops and rises back up.

Next, the resistance of the sample to this first cycle is observed.

If the sample has withstood this first cycle, the "rise and fall" cycle of the round-tipped metal rod is reproduced on the sample 5 times, said bead applying a force of 26 N to the sample at each cycle.

Results:

The table below summarizes the state of the sample of composite material after 1 and 5 test cycles:

| Products tested | Results |
| --- | --- |
| Sample using the self-supporting interface material according to the invention (1 cycle) | No breaking of the product. |
| Sample using the self-supporting interface material according to the invention (5 cycles) | No breaking of the product. |

Figure 5:
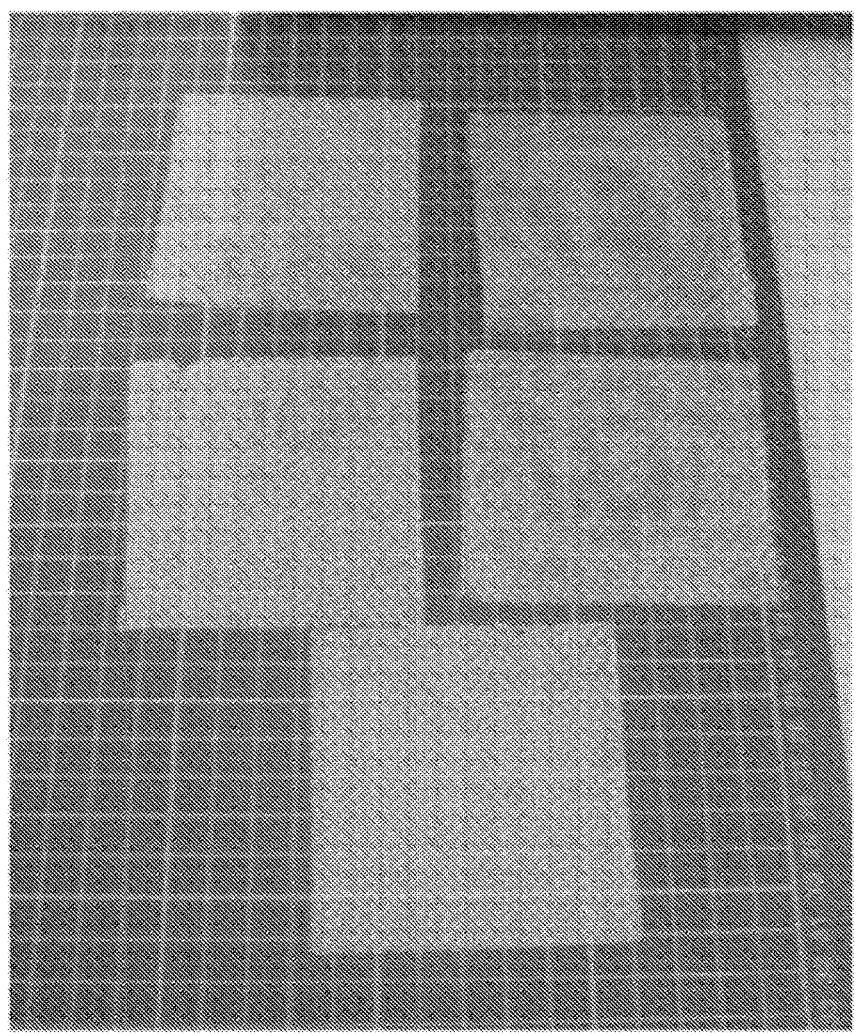
FIG. 5 is a photograph of the casing of the composite material according to the invention in the hydrated state after "5 cycles" of the mechanical strength test.

FIG. 5 illustrates the sample using the self-supporting interface material according to the invention after 5 test cycles. It is noted that the product undergoes only very slight deformations, and in no case does it become either entirely or partially destructured.

Said self-supporting interface material according to the invention is therefore a novel material, comparable to a non-stick gel, which may be used alone, that is to say without the need for a support to support it, as is described in applications WO2009/071928 and WO2009/071938. When it is tested in the form of a composite wound packing material, as in the present example, it has good pressure resistance under conditions comparable to those used in NPT.

The invention claimed is:

1. A composite wound packing material comprising a casing enclosing at least one material forming fluid flow channels, said casing being composed of a self-supporting interface material formed from a thin layer of a composition comprising a hydrophobic matrix and comprising through-holes, said hydrophobic matrix comprising:
   per 100 parts by weight of a styrene/saturated olefin/styrene triblock copolymer having a viscosity of between 0.2 and 2 Pa·s, as measured in a 10% (weight/weight) solution in toluene;
   from 400 to 1220 parts by weight of a plasticizer; and
   from 0 to 720 parts by weight of petroleum jelly;
wherein:
   the total amount of plasticizer and petroleum jelly is greater than or equal to 750 parts by weight; and
   the amount of petroleum jelly is between 400 and 720 parts by weight when the amount of plasticizer is between 1000 and 1220 parts by weight.

2. The composite wound packing material of claim 1, wherein the hydrophobic matrix comprises, per 100 parts by weight of the copolymer:
   from 600 to 900 parts by weight of a plasticizer; and
   from 150 to 450 parts by weight of petroleum jelly.

3. The composite wound packing material of claim 1, wherein the composition comprising a hydrophobic matrix further comprises hydrocolloid particles at an amount of less than or equal to 25% by weight relative to the total weight of said hydrophobic matrix.

4. The composite wound packing material of claim 1, wherein the casing made of self-supporting material is in the form of a breathable net or grid having a thickness of between 0.4 and 2 mm.

5. The composite wound packing material of claim 1, wherein the through-holes of the self-supporting interface material have any geometry and have a surface area between 0.25 and 5 mm$^2$; wherein the total surface area of said through-holes represents between 20% and 70% of the total surface area of said self-supporting interface material.

6. The composite wound packing material of claim 1 wherein the casing comprises a support formed from a fabric of yarns made of flexible, and non-elastic material; wherein the yarns constituting the fabric are hydrophobic in nature.

7. The composite wound packing material of claim 1 wherein the at least one material enclosed by the casing may be porous or non-porous, compressible or non-compressible, deformable or non-deformable, resilient or non-resilient.

8. The composite wound packing material of claim 1 wherein the at least one material enclosed by the casing is porous, compressible and resilient.

9. The composite wound packing material of claim 1, wherein the at least one material is an assembly of materials.

10. The composite wound packing material of claim 9 wherein the assembly of materials is porous, compressible and resilient.

11. The composite wound packing material of claim 9 wherein the assembly of materials is non-porous, non-compressible and non-deformable.

12. The composite wound packing material of claim 8, wherein the at least one porous, compressible and resilient material comprises one or more foams or gauzes having a hardness ranging from 5 to 100 Shore A.

13. The composite wound packing material of claim 8, wherein the at least one porous, compressible and resilient material comprises one or more foams or gauzes having a hardness ranging from 20 to 100 Shore A.

14. The composite wound packing material of claim 1, wherein the casing made of self-supporting material is in the form of a breathable net or grid having a thickness of between 0.5 and 1 mm.

15. The composite wound packing material of claim 1, wherein the casing made of self-supporting material is in the form of a breathable net or grid having a thickness of about 0.6 mm.

16. The composite wound packing material of claim 1, wherein the through-holes of the self-supporting interface material have a geometry selected from the group consisting of a circular, rectangular, trapezoidal and square cross section geometry.

17. The composite wound packing material of claim 1, wherein the through-holes of the self-supporting interface material have any geometry and have a surface area between 0.25 and 5 mm$^2$; wherein the total surface area of said through-holes represents between 30 and 50% of the total surface area of said self-supporting interface material.

18. The composite wound packing material of claim 6 wherein the yarns constituting the fabric are made of polyester.

19. The composite wound packing material of claim 18 wherein the yarns constituting the fabric are made of polyethylene terephthalate.

* * * * *